United States Patent

Zhi et al.

[11] Patent Number: 5,892,053
[45] Date of Patent: Apr. 6, 1999

[54] PROCESS FOR PREPARING 3-HALOALKYL-1H-PYRAZOLES

[75] Inventors: Benxin Zhi, Hoffman Estates; Murad Newaz, Palatine, both of Ill.

[73] Assignee: G. D. Searle & Co., Skokie, Ill.

[21] Appl. No.: 867,754

[22] Filed: Jun. 3, 1997

Related U.S. Application Data

[63] Continuation of Ser. No. 449,975, May 25, 1995, abandoned.

[51] Int. Cl.$^6$ .................................................. C07D 231/12
[52] U.S. Cl. ............................................................. 548/377.1
[58] Field of Search ............................................. 548/377.1

[56] References Cited

U.S. PATENT DOCUMENTS 5,344,992  9/1994  Drewes et al. .
5,466,823  11/1995  Talley et al. .......................... 548/377.1

FOREIGN PATENT DOCUMENTS 2041134  10/1991  Canada .
 418845  3/1991  European Pat. Off. .
 554829  8/1993  European Pat. Off. .
2429674  6/1974  Germany .
71/4221  6/1971  Saudi Arabia .
95/15316  6/1995  WIPO .

OTHER PUBLICATIONS

K. Joshi et al., Pharmazie, 34, 68–9 (1979).
K. Joshi et al., J. Ind. Chem., 60, 1074–6 (1983).
R. Ho. et al, Aust. J. Chem., 21, 1781–7 (1968).
T. Nishiwaki, Bull. Chem. Soc. Japan, 42, 3024–26 (1969).
J. Wright et al., J. Med. Chem., 7, 102–5 (1963).
R. Soliman and H. Feid–Allah, J. Pharm. Sci., 70, 602–5 (1980).

*Primary Examiner*—Robert W. Ramsuer
*Attorney, Agent, or Firm*—Joseph W. Bulock

[57] ABSTRACT

An efficient synthesis of 3-haloalkyl-1H-pyrazoles, suitable for adoption in a safe, large-scale process, has been developed.

14 Claims, No Drawings

PROCESS FOR PREPARING 3-HALOALKYL-1H-PYRAZOLES

This is a continuation of application Ser. No. 08/449,975 filed May 25, 1995 now abandoned.

BACKGROUND

Pyrazoles have been widely described as pharmaceutical therapeutic agents, including antiinflammatories, and antidiabetic agents, among others. More recently, [3-haloalkyl-1H-pyrazole-1-yl]benzenesulfonamide have been identified as potent antiinflammatories without the side effects commonly-associated with such antiinflammatory agents. It became apparent that there was no known method to prepare such compounds, especially in a commercially viable one-pot synthesis incorporating common starting materials and reagents.

The formation of halogenated 1-aryl-butane-1,3-diones has been described [K. Joshi et al., *Pharmazie*, 34, 68–9 (1979); K. Joshi et al., *J. Ind. Chem. Soc.*, 60, 1074–6 (1983); R. Yo and S. Livingstone, *Aust. J. Chem.*, 21, 1781–7 (1968); CA 2,041,134, ZA 7,104,221 and DE 2,429, 674].

In addition, the preparation of pyrazoles from the condensation of diketones and hydrazines has been described [EP 418,845, EP 554,829, T. Nishiwaki, *Bull. Chem. Soc. Japan*, 42, 3024–26 (1969); J. Wright et al., *J. Med. Chem.*, 7, 102–5 (1963); and R. Soliman and H. Feid-Allah, *J. Pharm. Sci.*, 70, 602–5 (1980)].

However, these preparations do not provide a scaleable commercial process. In addition, they require isolation of the intermediate diketone, which adds to the cost and complexity of the synthesis.

SUMMARY OF INVENTION

A scaleable procedure for the preparation of 1,3,4,5-substituted pyrazoles has not been previously described. Such pyrazoles have been indicated as having pharmaceutical activity including hypoglycemic activity and antiinflammatory activity.

This invention provides an efficient synthesis of 3-haloalkyl-1H-pyrazoles, suitable for adoption in a safe, large-scale process, and particularly for a one-pot synthesis.

DETAILED DEACRIPTION OF THE INVENTION

This invention relates to a method of preparing 3-haloalkyl-1H-pyrazoles comprising the steps of forming a 4-halo-phenyl-butane-1,3-dione (or the keto-enol tautomer thereof) and treating said dione with a benzenesulfonamide to form the [3-haloalkyl-1H-pyrazol-1-yl] benzenesulfonamide. Specifically, the invention relates to a method of forming antiinflammatory compounds of Formula I

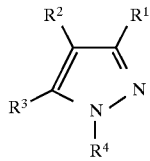

wherein $R^1$ is haloalkyl;
wherein $R^2$ is selected from selected from hydrido, alkyl, cyano, hydroxyalkyl, cycloalkyl, alkylsulfonyl and halo;
wherein $R^3$ is selected from cycloalkyl, cycloalkenyl, aryl and heteroaryl; wherein $R^3$ is optionally substituted at a substitutable position with one or more radicals selected from halo, alkylthio, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, heterocyclo and amino; and
wherein $R^4$ is aryl substituted at a substitutable position with aminosulfonyl;
the method comprising the steps of forming a 4-halo-1-phenyl-butane-1,3-dione by treating a ketone with a base and a haloalkyl ester, and forming the 3-haloalkyl-1H-pyrazoles by treating said dione with an appropriate aryl hydrazine, or a salt thereof.

Preferably, $R^1$ is lower haloalkyl; $R^2$ is selected from hydrido, lower alkyl, cyano, lower hydroxyalkyl, lower cycloalkyl, lower alkylsulfonyl and halo; $R^3$ is selected from lower cycloalkyl, lower cycloalkenyl, aryl and lower heteroaryl, wherein $R^3$ is optionally substituted at a substitutable position with one or more radicals selected from halo, cyano, nitro, hydroxyl, carboxyl, cycloalkyl, aminocarbonyl, lower alkylthio, lower alkyl, lower alkenyl, lower alkoxycarbonyl, lower haloalkyl, lower alkoxy, lower hydroxyalkyl, lower haloalkoxy, lower N-alkylamino, lower N,N-dialkylamino, 5- or 6-membered heterocyclo and amino; and $R^4$ is aryl substituted at a substitutable position with aminosulfonyl.

More preferably, $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl; wherein $R^2$ is selected from hydrido, methyl, ethyl, isopropyl, tert-butyl, isobutyl, hexyl, cyano, fluoro, chloro, bromo, methylsulfonyl, ethylsulfonyl, cyclopropyl, cyclopentyl, cyclobutyl, hydroxypropyl, hydroxymethyl, and hydroxypropyl; wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, indenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl and pyrazinyl; wherein $R^3$ is optionally substituted at a substitutable position with one or more radicals selected from fluoro, chloro, bromo, methylthio, methyl, ethyl, propyl, isopropyl, tert-butyl, isobutyl, hexyl, ethenyl, propenyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, aminosulfonyl, hydroxypropyl, hydroxyisopropyl, hydroxymethyl, hydroxyethyl, trifluoromethoxy, amino, N-methylamino, N-ethylamino, N-ethyl-N-methylamino, N,N-dimethylamino, N,N-diethylamino, piperidinyl, piperazinyl, morpholino, cyclohexyl, cyclopropyl, cyclobutyl, and nitro; and wherein $R^4$ is phenyl substituted at a substitutable position with aminosulfonyl; or a pharmaceutically acceptable salt thereof.

More specifically, the invention relates to a method of preparing compounds of Formula II

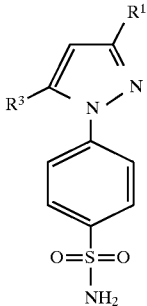

II the method comprising forming a diketone of Formula III

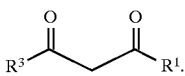

III by treating a ketone with a base and

and treating the diketone with a 4-(aminosulfonyl) phenyl-hydrazine or a salt thereof, in a suitable solvent;

wherein $R^1$ is haloalkyl; wherein $R^3$ is selected from cycloalkyl, cycloalkenyl, aryl and heteroaryl; wherein $R^3$ is optionally substituted at a substitutable position with one or more radicals selected from halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, aminosulfonyl, heterocyclo and amino; and wherein $R^5$ is lower alkyl.

Preferably, compounds of Formula II can be prepared wherein $R^1$ is selected from lower haloalkyl; wherein $R^3$ is selected from lower cycloalkyl, lower cycloalkenyl, aryl and 5- or 6-membered heteroaryl; wherein $R^3$ is optionally substituted at a substitutable position with one or more radicals selected from halo, cyano, nitro, hydroxyl, carboxyl, cycloalkyl, aminocarbonyl, aminosulfonyl, lower alkylthio, lower alkyl, lower alkenyl, lower alkylsulfonyl, lower alkoxycarbonyl, lower haloalkyl, lower alkoxy, lower hydroxyalkyl, lower haloalkoxy, lower N-alkylamino, lower N,N-dialkylamino, 5- or 6-membered heterocyclo and amino; and wherein $R^5$ is lower alkyl.

More preferably, the method can be used to prepare compounds wherein $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl; wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, indenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl and pyrazinyl; wherein $R^3$ is optionally substituted at a substitutable position with one or more radicals selected from fluoro, chloro, bromo, methylthio, methyl, ethyl, propyl, isopropyl, tert-butyl, isobutyl, hexyl, ethenyl, propenyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, aminosulfonyl, hydroxypropyl, hydroxyisopropyl, hydroxymethyl, hydroxyethyl, trifluoromethoxy, amino, N-methylamino, N-ethylamino, N-ethyl-N-methylamino, N,N-dimethylamino, N,N-diethylamino, piperidinyl, piperazinyl, morpholino, cyclohexyl, cyclopropyl, cyclobutyl, and nitro; and wherein $R^5$ is selected from methyl and ethyl.

More preferably, the method can be used to prepare compounds wherein $R^1$ is selected from trifluoromethyl, difluoromethyl, pentafluoroethyl and heptafluoropropyl; wherein $R^3$ is phenyl optionally substituted at a substitutable position with one or more substituents selected from fluoro, chloro, bromo, methyl, ethyl, methoxy, ethoxy, methylthio and hydroxyl.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkyl radicals are "lower alkenyl" radicals having two to about six carbon atoms. Examples of such radicals include ethenyl, n-propenyl, butenyl, and the like. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclo" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 5 to 6 membered heteromonocyclic group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino.

Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The term "arylsulfonyl" embraces aryl radicals as defined above, attached to a sulfonyl radical. Examples of such radicals include phenylsulfonyl. The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$). The terms "carboxy" or "carboxyl", whether used alone or with other terms, such as "carboxyalkyl", denotes —$CO_2H$. The terms "alkanoyl" or "carboxyalkyl" embrace radicals having a carboxy radical as defined above, attached to an alkyl radical. The alkanoyl radicals may be substituted or unsubstituted, such as formyl, acetyl, propionyl (propanoyl), butanoyl (butyryl), isobutanoyl (isobutyryl), valeryl (pentanoyl), isovaleryl, pivaloyl, hexanoyl or the like. The term "carbonyl", whether used alone or with other terms, such as "alkylcarbonyl", denotes —(C=O)—. The term "alkylcarbonyl" embraces radicals having a carbonyl radical substituted with an alkyl radical. More preferred alkylcarbonyl radicals are "lower alkylcarbonyl" radicals having one to six carbon atoms. Examples of such radicals include methylcarbonyl and ethylcarbonyl. The term "alkylcarbonylalkyl", denotes an alkyl radical substituted with an "alkylcarbonyl" radical. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)$NH_2$. The term "aminoalkyl" embraces alkyl radicals substituted with amino radicals. The term "alkylaminoalkyl" embraces aminoalkyl radicals having the nitrogen atom substituted with an alkyl radical. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, halkoalkyl and haloalkoxy. The terms benzyl and phenylmethyl are interchangeable. The term "cycloalkyl" embraces radicals having three to ten carbon atoms. More preferred cycloalkyl radicals are "lower cycloalkyl" radicals having three to seven carbon atoms.

Examples include radicals such as cyclopropyl, cyclobutyl, cyclopentyl, cyclohexyl and cycloheptyl. The term "cycloalkenyl" embraces unsaturated cyclic radicals having three to ten carbon atoms, such as cyclobutenyl, cyclopentenyl, cyclohexenyl and cycloheptenyl. The term "alkylthio" embraces radicals containing a linear or branched alkyl radical, of one to ten carbon atoms, attached to a divalent sulfur atom. An example of "alkylthio" is methylthio, ($CH_3$—S—). The term "alkylsulfinyl" embraces radicals containing a linear or branched alkyl radical, of one to ten carbon atoms, attached to a divalent —S(=O)— atom. The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" denotes amino groups which have been substituted with one or two aralkyl radicals, such as N-benzylamino. The term "acyl", whether used alone, or within a term such as "acylamino", denotes a radical provided by the residue after removal of hydroxyl from an organic acid. The term "ester" includes alkylated carboxylic acids or their equivalents, such as (RCO-imidazole).

GENERAL SYNTHETIC PROCEDURES

A general Scheme for the preparation of antiinflammatory pyrazoles of Formulas I–II are shown in the following Schemes where $R^1$–$R^5$ are as previously defined.

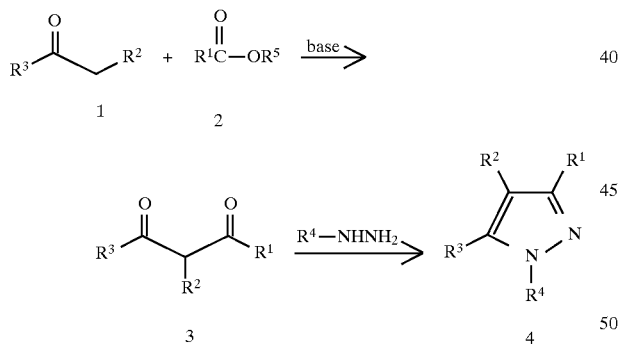

Synthetic Scheme I shows the two steps of the present method. In step one, the diketone 3 is formed, such as by treatment of ketone 1 with base and ester 2 in a suitable solvent. In step 2, the diketone 3 is condensed with the hydrazine to form pyrazole 4.

Suitable bases include alkali metal alcoholates and alkaline earth metal alcoholates. Examples of alkali metal alcoholates include lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, lithium butoxide, sodium butoxide, potassium butoxide, lithium isobutoxide, sodium isobutoxide, potassium isobutoxide, lithium tert-butoxide, sodium tert-butoxide, potassium tert-butoxide, lithium pentoxide, sodium pentoxide, and potassium pentoxide. Examples of alkaline earth metal alkoxides include calcium dimethoxide, magnesium dimethoxide, calcium diethoxide, magnesium diethoxide, calcium dipropoxide, magnesium dipropoxide, calcium di(isopropoxide), magnesium di(isopropoxide), calcium dibutoxide, magnesium dibutoxide, calcium di(isobutoxide), and magnesium di(isobutoxide).

Preferably, alkali metal alcoholates are used, and more preferably, sodium methoxide.

Suitable solvents include organic solvents which are inert under the reaction conditions, ethers, aliphatic or aromatic hydrocarbons, cyclic or linear amides and alcohols, for example. Examples of such ethers include diethyl ether, diisopropyl ether, dibutyl ether, ethylene glycol dimethyl ether, diethylene glycol dimethyl ether, dioxane, tetrahydrofuran, tetrahydropyran and methyl tert-butyl ether (MTBE). Cyclic ethers and higher molecular weight linear ethers are preferred, and MTBE is more preferred. Mixtures of these solvents may also be used. Examples of such hydrocarbons include pentane, hexane, heptane, petroleum ethers, benzene, toluene and xylene. An example of a cyclic or linear amide is N-methyl-pyrrolidone. Examples of such alcohols include ethanol and isopropanol.

Excess amounts of the reagents, specifically the ester and aryl hydrazine can be used, although equimolar amounts are preferred.

The reaction takes place at relatively low reaction temperatures. For example, the diketone can be formed at a temperature range of about 15° to about 70° C. Preferably it is formed at a temperature of about 20° to about 60° C. The pyrazole is preferably formed at reflux temperature. More preferably, it is formed at a temperature of about 50° to about 60° C.

Preferably, the pH of the reaction mixture is below 7 before the hydrazine is added. More preferably, aqueous HCl is added before the hydrazine is added.

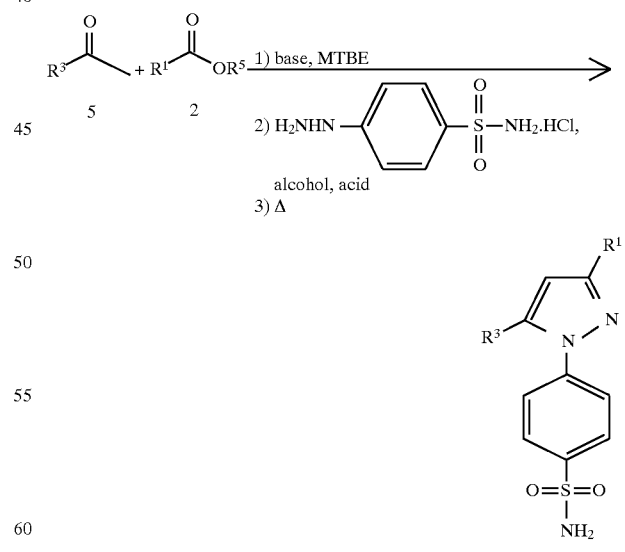

Synthetic Scheme II shows a method of forming 4-[3-haloalkyl-1H-pyrazol-1-yl]benzenesulfonamides. In step one, the diketone 3 is formed, such as by treatment of ketone 5 with base and ester 2 in a suitable solvent. The diketone 3 is condensed, without isolation or further purification, with the hydrazine to form pyrazole 6.

Suitable bases include alkali metal alcoholates. Examples of alkali metal alcoholates include lithium methoxide, sodium methoxide, potassium methoxide, lithium ethoxide, sodium ethoxide, potassium ethoxide, and lithium propoxide. Preferably, sodium methoxide is used.

Suitable solvents for the diketone formation step include organic solvents which are inert under the reaction conditions, ethers, for example. Examples of such ethers include diethyl ether, diisopropyl ether, dibutyl ether, ethylene glycol dimethyl ether, diethylene glycol dimethyl ether, dioxane, tetrahydrofuran, tetrahydropyran and methyl tert-butyl ether (MTBE). Cyclic ethers and higher molecular weight linear ethers are preferred, and MTBE is more preferred. Mixtures of these solvents may also be used. Suitable solvents for the pyrazole-forming step include aqueous-miscible solvents, such as alcohols and organic acids. Examples of such alcohols include ethanol and isopropanol.

Excess amounts of the reagents, specifically the ester and aryl hydrazine can be used, although equimolar amounts are preferred.

The reaction takes place at relatively low reaction temperatures. For example, the diketone can be formed at a temperature range of about 15° to about 70° C. Preferably it is formed at a temperature of about 20° to about 60° C. The pyrazole is preferably formed at reflux temperature. More preferably, it is formed at a temperature of about 50° to about 60° C.

Preferably, the pH of the reaction mixture is below 7 before the hydrazine is added. More preferably, aqueous HCl is added before the hydrazine is added.

A further advantage of the present process is that materials can be carried through the above steps without purification of the intermediate compounds. However, if purification is desired, the intermediates disclosed can be isolated.

The following examples contain detailed descriptions of the methods of preparation of pyrazoles of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1
4-[5-(4-Methylphenyl)-3-trifluoromethyl-1H-pyrazol-1-yl]benzenesulfonamide To a solution of ethyl trifluoroacetate (1.90 ml, 16.0 mmol) in 7 ml of MTBE was added 25% NaOMe (3.62 ml, 16.8 mmol). Next 4'-chloroaceteophenone (2.08 ml, 16.0 mmol) in 2 ml of MTBE was added. The mixture was stirred at room temperature overnight. To above solution was added 100 ml of 90% EtOH, followed by 4N HCl (4.0 ml, 16 mmol) and 4-sulphonamidophenylhydrazine hydrochloride (3.58 g, 16 mmol). The mixture was heated to reflux for 3 hours. The mixture was concentrated. When 30 ml of water was added, a solid formed. The solid was filtered and washed with 20 ml of 60% EtOH to give 4.50 g of white solid. The filtrate was evaporated and taken up in ethyl acetate (100 ml), washed with sat. NaHCO$_3$, and brine, dried over MgSO$_4$, and concentrated. Heptane was added at boiling point of the mixture. After cooling down to 0° C., 1.01 g more product was obtained. The combined yield of the first two crops was 86%.

EXAMPLE 2
4-[5-(3-Fluoro-4-methoxyphenyl)-3-difluoromethyl-1H-pyrazol-1-yl]benzenesulfonamide To a solution of 4'-methoxy-3'-fluoroacetophenone (21.5 g, 128 mmol) in 137 ml of methyl t-butyl ether (MTBE) was added ethyl difluoroacetate (16.6 ml, 166 mmol) at 25° C. Sodium methoxide (25 wt%) in methanol (35.0 ml, 154 mmol) was added. The mixture was heated to reflux for 3 hours (pot temperature reached to 54° C. in 15 minutes). Prepare a slurry of 4-sulphonamidophenylhydrazine hydrochloride 28.6 g, 128 mmol in 200 ml of EtOH. To above solution was added water (246 ml), 37% HCl (12.8 ml, 154 mmol) and 4-sulphonamidophenylhydrazine hydrochloride (3.58 g, 16 mmol) in 200 ml EtOH. The mixture was heated to reflux for 3 hours (pot temperature reached 62° C.). The solution was cooled to 5±5° C. to precipitate the product which was filtered and washed with water. The product was recrystallized from ethyl acetate and water to give a white solid (39.95 g, mp 162–163° C.).

From the foregoing detailed description, one skilled in the art can easily ascertain the essential characteristics of this invention, and without departing from the spirit and scope thereof, can make various changes and modifications of the invention to adapt it to various usages and conditions.

What is claimed is:

1. A process for preparing compounds of Formular II

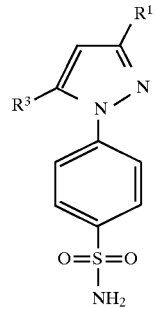

the process comprising forming a diketone of Formular III

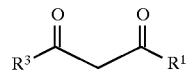

by treating a compound of the formular

with a base and

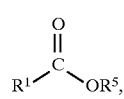

and treating said diketon, in a suitable solvent comprising an aqueous mixture of alcohol and acid, with 4-(aminosulfonyl) phenylhydrazine or a salt thereof;

wherein $R^1$ is haloalkyl; wherein $R^3$ is selected from cycloalkyl, cycloalkenyl, aryl and heteroaryl; wherein $R^3$ is optionally substituted at a sustitutable position with one or more radicals selected from halo, alkylthio, alkylsulfonl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, aminosulfonyl, heterocyclo and amino; and wherein $R^5$ is lower alkyl.

2. The process of claim 1 wherein the 4-aminosulfonylphenylhydrazine is 4-(aminosulfonyl)phanylhydrazine, hydrochloride salt.

3. The process of claim 1 wherein the haloalkylester is selected from ethyltrifluoroacetate, methyltrifluoroacetate, methyldifluoroacetate, ethyldifluoroacetate, ethyl pentafluoropropionate, ethyl heptafluorobutyrate, and methyl 2-chloro-2,2-difluoroacetate.

4. The process of claim 1 wherein the base is an alkali metal alcoholate.

5. The process of claim 4 wherein the base is sodium methoxide.

6. The process of claim 1 wherein $R^1$ is lower haloalkyl; wherein $R^3$ is selected from lower cycloalkyl, lower cycloalkenyl, aryl and 5- or 6-membered heteroaryl; wherein $R^3$ is optionally substituted at a substitutable position with one or more radicals selected from halo, cyano, nitro, hydroxyl, carboxyl, cycloalkyl, aminocarbonyl, lower alkylthio, lower alkyl, lower alkenyl, lower alkoxycarbonyl, lower haloalkyl, lower alkoxy, lower hydroxyalkyl, lower haloalkoxy, lower N-alkylamino, lower N,N-dialkylamino, 5- or 6-membered heterocyclo and amino; and wherein $R^5$ is lower alkyl.

7. The process of claim 6 wherein $R^1$ is selected from fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl; wherein $R^3$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, indenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl and pyrazinyl;.wherein $R^3$ is optionally substituted at a substitutable position with one or more radicals selected from fluoro, chloro, bromo, methylthio, methyl, ethyl, propyl, isopropyl, tert-butyl, isobutyl, hexyl, ethylenyl, propenyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxypropyl, hydroxyisopropyl, hydroxymethyl, hydroxyethyl, trifluoromethoxy, amino, N-methylamino, N-ethylamino, N-ethyl-N-methylamino, N,N-dimethylamino, N,N-diethylamino, piperidinyl, piperazinyl, morpholino, cyclohexyl, cyclopropyl, cyclobutyl, and nitro; and wherein $R^5$ is selected from methyl and ethyl.

8. The process of claim 7 wherein $R^1$ is selected from trifluoromethyl, difluoromethyl, pentafluoromethyl and heptafluoropropyl; and wherein $R^3$ is phenyl optionally substituted at a substitutable position with one or more substituents selected from fluoro, chloro, bromo, methyl, ethyl, methoxy, ethoxy, methylthio and hydroxyl.

9. The process of claim 8 wherein the compound is 4-[5-(4-methylphenyl)-3-trifluoromethyl-1H-pyrazol-1-yl]benzenesulfonamide.

10. The process of claim 8 wherein the compound is 4-[5-(3-fluoro-4methoxyphenyl) -3-difluoromethyl-1H-pyrazol-1-yl]benzenesulfonamide.

11. The process of claim 1 wherein the solvent is selected from ethers, alcohols and an aqueous mixture thereof.

12. The process of claim 11 wherein the solvent is a mixture of methyl tert-butyl ether and aqueous ethanol.

13. A process for preparing compounds of Formula II

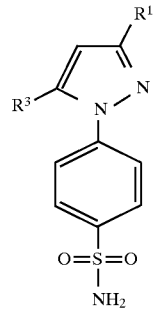

wherein $R^1$ is selected from trifluoromethyl, difluoromethyl, pentafluoromethyl and heptafluoropropyl; and wherein $R^3$ is phenyl optionally substituted at a substitutable position with one or more substituents selected from fluoro, chloro, bromo, methyl, ethyl, methoxy, ethoxy, methylthio and hydroxyl; the process comprising the steps of (a) mixing, in methyl tert-butyl ether, an acetophenone

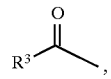

an alkyl haloacetate

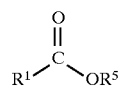

wherein $R^5$ is ethyl, and sodium methoxide, and (b) treating the mixture with aqueous hydrochloric acid, ethanol and 4-(aminosulfonyl)phenylhydrazine, or a salt thereof.

14. The process of claim 13 wherein the acetophenone is selected from 4'-chloroacetophenone, 4'-methylacetophenone, 3'-fluoro-4'-methoxyacetophenone and 4'-fluoroacetophenone, and wherein $R^1$ is trifluoromethyl or difluoromethyl.

* * * * *